US012796932B2

(12) United States Patent
Ding et al.

(10) Patent No.: US 12,796,932 B2
(45) Date of Patent: Nov. 17, 2026

(54) MAGNETIC RESONANCE IMAGING METHOD AND MAGNETIC RESONANCE IMAGING SYSTEM

(71) Applicant: GE Precision Healthcare LLC, Waukesha, WI (US)

(72) Inventors: Yao Ding, Beijing (CN); Liangliang Li, Beijing (CN); Yongchuan Lai, Beijing (CN); Xiaocheng Wei, Beijing (CN)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 19/266,914

(22) Filed: Jul. 11, 2025

(65) Prior Publication Data

US 2026/0013730 A1 Jan. 15, 2026

(30) Foreign Application Priority Data

Jul. 12, 2024 (CN) ......................... 202410934735.5

(51) Int. Cl.
*A61B 5/00* (2006.01)
*A61B 5/055* (2006.01)

(52) U.S. Cl.
CPC ............ *A61B 5/0044* (2013.01); *A61B 5/055* (2013.01); *A61B 5/7292* (2013.01)

(58) Field of Classification Search
CPC ...... A61B 5/0044; A61B 5/055; A61B 5/7292
See application file for complete search history.

(56) References Cited

U.S. PATENT DOCUMENTS 9,081,073 B2 7/2015 Rehwald
2020/0041591 A1* 2/2020 Weingartner .......... A61B 5/055
2022/0117508 A1* 4/2022 Dharmakumar ......... A61B 5/00

OTHER PUBLICATIONS

Keegan J, Gatehouse PD, Haldar S, Wage R, Babu-Narayan SV, Firmin DN. Dynamic inversion time for improved 3D late gadolinium enhancement imaging in patients with atrial fibrillation. Magn Reson Med. Feb. 2015; (Year: 2015).*

(Continued)

*Primary Examiner* — Pascal M Bui Pho
*Assistant Examiner* — Nicholas A Robinson

(57) ABSTRACT

A magnetic resonance imaging method and a magnetic resonance imaging system is provided. The method is used to acquire, in a plurality of consecutive time units, magnetic resonance signals representing one or more layers of an anatomical region of interest of a subject and generate a magnetic resonance image. The method includes: determining an effective repetition time of an $(N-1)^{th}$ time unit; determining the position of an inversion recovery pulse in an $N^{th}$ time unit based on the effective repetition time of the $(N-1)^{th}$ time unit, wherein N is an integer greater than 1; transmitting, in the $N^{th}$ time unit, a scan sequence generated based on the position of the inversion recovery pulse, and acquiring a magnetic resonance signal representing an anatomical region of interest of a subject; and reconstructing a magnetic resonance image at least based on the magnetic resonance signal.

14 Claims, 8 Drawing Sheets

(56) References Cited

OTHER PUBLICATIONS

Krishnamurthy, R., Pednekar, A., Smink, J. et al. Arrhythmia insensitive inversion recovery preparation (IR-prep) with real-time adaptive inversion delay (TI):phantom validation. J Cardiovasc Magn Reson 12 (Suppl 1), p. 168 (2010). (Year: 2010).*
J. Oster, O. Pietquin, G. Bosser and J. Felblinger, "Adaptive RR prediction for cardiac MRI," 2008 IEEE International Conference on Acoustics, Speech and Signal Processing, Las Vegas, NV, USA, 2008 (Year: 2008).*
Oster et al "Adaptive Prediction of RR interval for online MR parameters changes" Proc. Intl. Soc. Mag. Reson. Med. 15 (2007) (Year: 2007).*
Oster et al "Adaptive Heart Rate Prediction for Black-Blood Systolic Imaging"; Proc. Intl. Soc. Mag. Reson. Med. 17 (2009) (Year: 2009).*
Burakiewicz et al., "Reducing artefacts in inversion recovery prepared MRI caused by varying heart rate through real-time adaptation of the inversion time", 19th Annual ISMRM Meeting, 2011, 1 page.
Keegan et al., "Dynamic inversion time for improved 3D late gadolinium enhancement imaging in patients with atrial fibrillation", MRM, 73: 646-654(2015), 19 pages.
Taigang He, et al, "Development of a novel optimized breathhold technique for myocardial T2 measurement in thalassemia", JMRI, 24(3), 580-585(2006), 6 pages.

* cited by examiner

MAGNETIC RESONANCE IMAGING METHOD AND MAGNETIC RESONANCE IMAGING SYSTEM

CROSS REFERENCE TO RELATED APPLICATIONS

The present application claims priority and benefit of Chinese Patent Application No. 202410934735.5 filed on Jul. 12, 2024, which is incorporated herein by reference in its entirety.

TECHNICAL FIELD

Embodiments of the present application relate to the technical field of medical devices, and in particular to a magnetic resonance imaging method and a magnetic resonance imaging system.

BACKGROUND

Magnetic resonance (MR) imaging systems are widely used in the field of medical diagnosis. A magnetic resonance imaging system generally has a main magnet, a gradient amplifier, a radio-frequency amplifier, a gradient coil, a transmit chain module, a transmit/receive coil, a receive chain module, etc. The transmit chain module generates a pulse signal and transmits the same to the transmit/receive coil; the transmit/receive coil generates a radio-frequency excitation signal to excite a scanned subject to generate a magnetic resonance signal; and after the excitation ends, by means of spatial encoding, the transmit/receive coil acquires the magnetic resonance signal, and fills the magnetic resonance signal into a k-space so that a medical image is reconstructed.

One common clinical application of magnetic resonance technology is cardiac imaging. Delayed enhancement is a very important technique in cardiac imaging, and is considered the gold standard for evaluating myocardial activity in cardiac magnetic resonance (CMR). In the delayed enhancement technique, a gadolinium contrast agent is injected into a patient, and after a certain time delay (10-30 min), a signal of a myocardial infarction or fibrosis region can be strengthened (enhanced), so that the position and the size of a lesion can be visually seen.

SUMMARY OF THE INVENTION

Embodiments of the present application provide a magnetic resonance imaging method and a magnetic resonance imaging system.

According to an aspect of the embodiments of the present application, a magnetic resonance imaging method is provided for acquiring magnetic resonance signals representing one or more layers of an anatomical region of interest of a subject over a plurality of consecutive time units and generating a magnetic resonance image. The method comprises determining an effective repetition time of an $(N-1)^{th}$ time unit; determining the position of an inversion recovery pulse in an $N^{th}$ time unit based on the effective repetition time of the $(N-1)^{th}$ time unit, where N is an integer greater than 1; transmitting, in the $N^{th}$ time unit, a scan sequence generated based on the position of the inversion recovery pulse and acquiring a magnetic resonance signal representing the anatomical region of interest; and reconstructing a magnetic resonance image at least based on the acquired magnetic resonance signal.

According to an aspect of the embodiments of the present application, a magnetic resonance imaging system is provided, comprising a scanning unit and a controller configured to perform the magnetic resonance imaging method described in the preceding aspect.

One of the beneficial effects of the embodiments of the present application is that: the position of the inversion recovery pulse in the $N^{th}$ time unit is determined based on the effective repetition time of the $(N-1)^{th}$ time unit. Therefore, dynamic updating of inversion times (TI) of various types of myocardial delayed enhancement sequences is supported, so that the sequences are not easily affected by heartbeat fluctuations or heart rate abnormalities, ghosting is reduced, and a myocardial suppression effect and image quality are improved.

With reference to the following description and drawings, specific implementations of the embodiments of the present application are disclosed in detail, and the way in which the principles of the embodiments of the present application can be employed are illustrated. It should be understood that the embodiments of the present application are not limited in scope thereby. Within the scope of the spirit and clauses of the appended claims, the embodiments of the present application comprise many changes, modifications, and equivalents.

BRIEF DESCRIPTION OF THE DRAWINGS

The included drawings are used to provide further understanding of the embodiments of the present application, which constitute a part of the description and are used to illustrate the implementations of the present application and explain the principles of the present application together with textual description. Evidently, the drawings in the following description are merely some embodiments of the present application, and those of ordinary skill in the art may obtain other implementations according to the drawings without involving inventive effort. In the drawings.

DETAILED DESCRIPTION

The aforementioned and other features of the embodiments of the present application will become apparent from the following description with reference to the drawings. In the description and drawings, specific implementations of the present application are disclosed in detail, and part of the implementations in which the principles of the embodiments of the present application may be employed are indicated. It should be understood that the present application is not limited to the described implementations. On the contrary, the embodiments of the present application include all modifications, variations, and equivalents which fall within the scope of the appended claims.

In the embodiments of the present application, the terms “first” and “second” etc., are used to distinguish different elements, but do not represent a spatial arrangement or temporal order, etc., of these elements, and these elements should not be limited by these terms. The term “and/or” includes any and all combinations of one or more associated listed terms. The terms “comprise”, “include”, “have”, etc., refer to the presence of described features, elements, components, or assemblies, but do not exclude the presence or addition of one or more other features, elements, components, or assemblies.

In the embodiments of the present application, the singular forms “a” and “the”, etc., include plural forms, and should be broadly construed as “a type of” or “a class of” rather than being limited to the meaning of “one”. Furthermore, the term “the” should be construed as including both the singular and plural forms, unless otherwise specified in the context. In addition, the term “according to” should be construed as “at least in part according to . . . ” and the term “on the basis of” should be construed as “at least in part on the basis of . . . ”, unless otherwise specified in the context.

The features described and/or illustrated for one implementation may be used in one or more other implementations in the same or similar way, be combined with features in other embodiments, or replace features in other implementations. The term “include/comprise” when used herein refers to the presence of features, integrated components, steps, or assemblies, but does not preclude the presence or addition of one or more other features, integrated components, steps, or assemblies.

Figure 1:
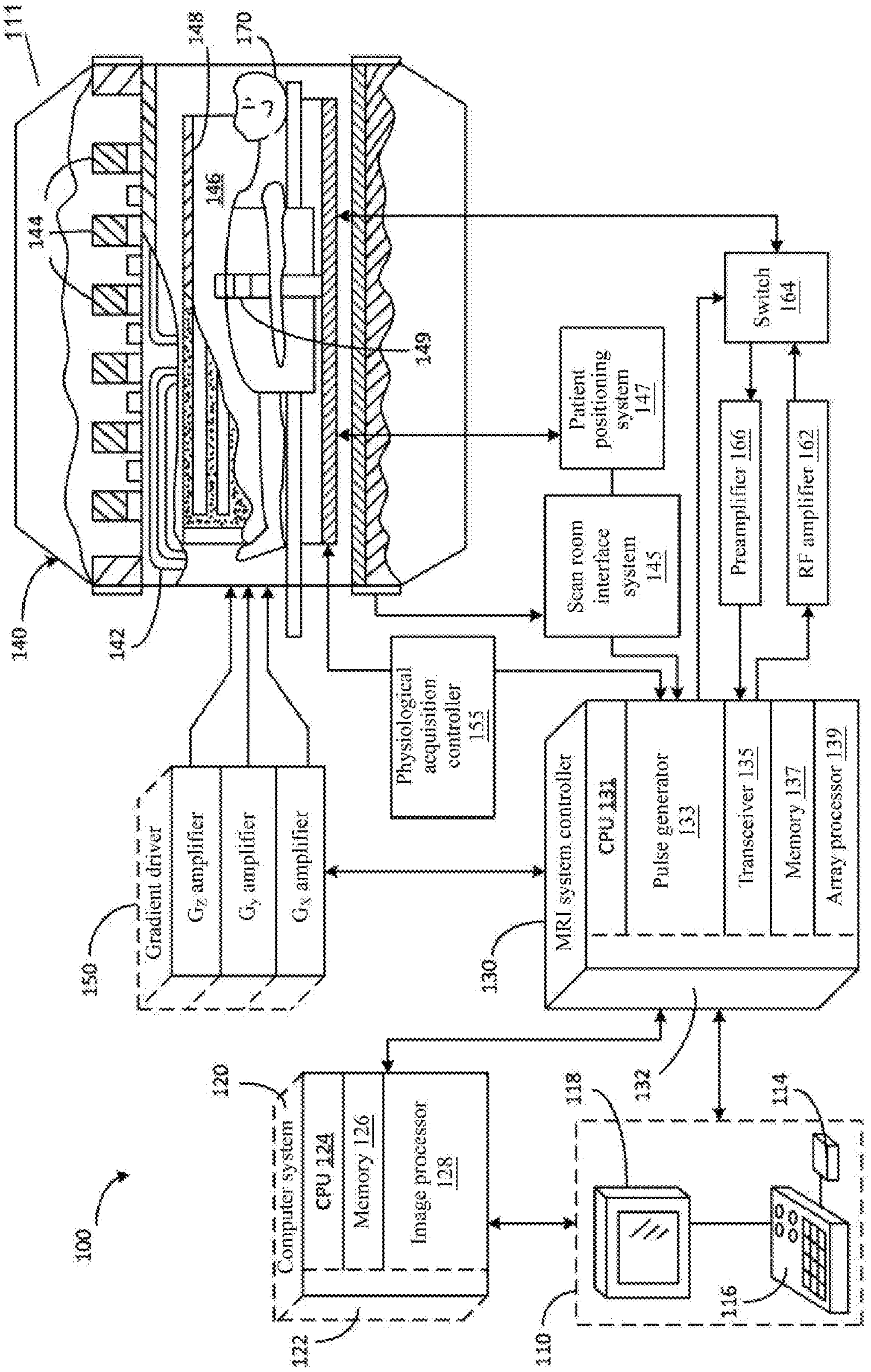
FIG. 1 is a schematic diagram of a magnetic resonance imaging system according to an embodiment of the present application.

For ease of understanding, FIG. 1 shows a magnetic resonance imaging (MRI) system 100 according to some embodiments of the present invention.

The MRI system 100 includes a scanning unit 111. The scanning unit 111 is used to perform a magnetic resonance scan of a subject (e.g., a human body) 170 to generate image data of a region of interest of the subject 170, wherein the region of interest may be a pre-determined anatomical site or anatomical tissue.

The operation of the MRI system 100 is controlled by an operator workstation 110 that includes an input device 114, a control panel 116, and a display 118. The input device 114 may be a joystick, a keyboard, a mouse, a trackball, a touch-activated screen, voice control, or any similar or equivalent input device. The control panel 116 may include a keyboard, a touch-activated screen, voice control, a button, a slider, or any similar or equivalent control device. The operator workstation 110 is coupled to and in communication with a computer system 120 that enables an operator to control the generation and display of images on the display 118. The computer system 120 includes various components that communicate with one another by means of an electrical and/or data connection module 122. The connection module 122 may employ a direct wired connection, a fiber optic connection, a wireless communication link, etc. The computer system 120 may include a central processing unit (CPU) 124, a memory 126, and an image processor 128. In some embodiments, the image processor 128 may be replaced by image processing functions implemented in the CPU 124. The computer system 120 may be connected to an archive media device, a persistent or backup memory, or a network. The computer system 120 may be coupled to and communicates with a separate MRI system controller 130.

The MRI system controller 130 includes a set of components that communicate with one another via an electrical and/or data connection module 132. The connection module 132 may employ a direct wired connection, a fiber optic connection, a wireless communication link, etc. The MRI system controller 130 may include a CPU 131, a sequence pulse generator 133 which is in communication with the operator workstation 110, a transceiver (or an RF transceiver) 135, a memory 137, and an array processor 139. In some embodiments, the sequence pulse generator 133 may be integrated into a resonance assembly 140 of the scanning unit 111 of the MRI system 100. The MRI system controller 130 may receive a command from the operator workstation 110, and is coupled to the scanning unit 111 to indicate an MRI scanning sequence to be performed during an MRI scan, so as to be used to control the scanning unit 111 to perform the flow of the aforementioned magnetic resonance scan. The MRI system controller 130 is further coupled to and in communication with a gradient driver system 150, which is coupled to a gradient coil assembly 142 to generate a magnetic field gradient during the MRI scan.

The sequence pulse generator 133 may further receive data from a physiological acquisition controller 155, which receives signals from a number of different sensors (such as electrocardiogram (ECG) signals from electrodes attached to a patient), which are connected to the subject or patient 170 undergoing an MRI scan. The sequence pulse generator 133 is coupled to and in communication with a scan room interface system 145 that receives signals from various sensors associated with the state of the resonance assembly 140. The scan room interface system 145 is further coupled to and in communication with a patient positioning system 147 that sends and receives signals to control movement of a patient table to a desired position to perform the MRI scan.

The MRI system controller 130 provides gradient waveforms to the gradient driver system 150, and the gradient driver system includes $G_x$ (x direction), $G_y$ (y direction), and $G_z$ (z direction) amplifiers, etc. Each of the $G_x$, $G_y$, and $G_z$ gradient amplifiers excites a corresponding gradient coil in the gradient coil assembly 142, so as to generate a magnetic field gradient used to spatially encode an MR signal during an MRI scan. The gradient coil assembly 142 is disposed within the resonance assembly 140, and the resonance assembly further includes a superconducting magnet having a superconducting coil 144 that, in operation, provides a static uniform longitudinal magnetic field $B_0$ throughout a cylindrical imaging volume 146. The resonance assembly 140 further includes an RF body coil 148, which, in operation, provides a transverse magnetic field $B_1$, the transverse magnetic field $B_1$ being substantially perpendicular to $B_0$ throughout the entire cylindrical imaging volume 146. The resonance assembly 140 may further include an RF surface coil 149 for imaging different anatomical structures of the patient undergoing the MRI scan. The RF body coil 148 and the RF surface coil 149 may be configured to operate in a transmit and receive mode, a transmit mode, or a receive mode.

The x direction may also be referred to as a frequency encoding direction or a $k_x$ direction in the k-space. The y direction may be referred to as a phase encoding direction or a $k_y$ direction in the k-space. $G_x$ can be used for frequency encoding or signal readout, and is generally referred to as a frequency encoding gradient or a readout gradient. $G_y$ can be used for phase encoding, and is generally referred to as a phase encoding gradient. $G_z$ can be used for slice (layer) position selection to obtain k-space data. It should be noted that a layer selection direction, a phase encoding direction, and a frequency encoding direction may be modified according to actual requirements.

The subject or patient 170 of the MRI scan may be positioned within the cylindrical imaging volume 146 of the resonance assembly 140. The transceiver 135 in the MRI system controller 130 generates RF excitation pulses that are amplified by an RF amplifier 162 and provided to the RF body coil 148 through a transmit/receive switch (T/R switch) 164.

As described above, the RF body coil 148 and the RF surface coil 149 may be used to transmit RF excitation pulses and/or receive resulting MR signals from the patient undergoing the MRI scan. The MR signals emitted by excited nuclei in the patient of the MRI scan may be sensed and received by the RF body coil 148 or the RF surface coil 149 and sent back to a preamplifier 166 through the T/R switch 164. The T/R switch 164 may be controlled by a signal from the sequence pulse generator 133 to electrically connect the RF amplifier 162 to the RF body coil 148 in the transmit mode and to connect the preamplifier 166 to the RF body coil 148 in the receive mode. The T/R switch 164 may further enable the RF surface coil 149 to be used in the transmit mode or the receive mode.

In some embodiments, the MR signals sensed and received by the RF body coil 148 or the RF surface coil 149 and amplified by the preamplifier 166 are stored in the memory 137 for post-processing as a raw k-space data array. A reconstructed magnetic resonance image may be obtained by transforming/processing the stored raw k-space data.

In some embodiments, the MR signals sensed and received by the RF body coil 148 or the RF surface coil 149 and amplified by the preamplifier 166 are demodulated, filtered, and digitized in a receiving portion of the transceiver 135, and transmitted to the memory 137 in the MRI system controller 130. For each image to be reconstructed, the data is rearranged into separate k-space data arrays, and each of said separate k-space data arrays is input to the array processor 139, the array processor being operated to transform the data into an array of image data by Fourier transform.

The array processor 139 uses transform methods, most commonly Fourier transform, to create images from the received MR signals. These images are transmitted to the computer system 120 and stored in the memory 126. In response to commands received from the operator workstation 110, the image data may be stored in a long-term memory, or may be further processed by the image processor 128 and transmitted to the operator workstation 110 for presentation on the display 118.

In various embodiments, components of the computer system 120 and the MRI system controller 130 may be implemented on the same computer system or on a plurality of computer systems. It should be understood that the MRI system 100 shown in FIG. 1 is intended for illustration. Suitable MRI systems may include more, fewer, and/or different components.

The MRI system controller 130 and the image processor 128 may separately or collectively include a computer processor and a storage medium. The storage medium records a predetermined data processing program to be executed by the computer processor. For example, the storage medium may store a program used to implement scanning processing (such as a scan flow and an imaging sequence), image reconstruction, image processing, etc. For example, the storage medium may store a program used to implement the magnetic resonance imaging method according to the embodiments of the present invention. The described storage medium may include, for example, a ROM, a floppy disk, a hard disk, an optical disk, a magneto-optical disk, a CD-ROM, or a non-volatile memory card.

The aforementioned "imaging sequence" (also referred to below as a scanning sequence or a pulse sequence) refers to a combination of pulses having specific amplitudes, widths, directions, and time sequences and applied when a magnetic resonance imaging scan is executed. These pulses may typically include, for example, radio-frequency pulses and gradient pulses. The radio-frequency pulses may include, for example, radio-frequency excitation pulses, radio-frequency refocusing pulses, inverse recovery pulses, etc. The gradient pulses may include, for example, the aforementioned gradient pulse used for layer selection, gradient pulse used for phase encoding, gradient pulse used for frequency encoding, gradient pulse used for phase shifting (phase shift), gradient pulse used for dispersion of phases (dephasing), etc.

Typically, a plurality of scan sequences can be preset in the magnetic resonance system, so that the sequence suitable for clinical detection requirements can be selected. The clinical detection requirements may include, for example, an imaging site, an imaging function, an imaging effect, and the like.

For ease of understanding, the principle of the myocardial delayed enhancement technique in magnetic resonance imaging is briefly described below.

During cardiac scanning, a contrast agent (gadolinium contrast agent) may be intravenously injected into a subject, and the heart is scanned after waiting for 10-30 minutes. Normal myocardium is characterized by "fast in and fast out", and the contrast agent is basically cleared 10-30 minutes after the contrast agent is injected. Delayed enhancement is displayed as a low signal. For abnormal myocardium (fibrosis, scar, infarction), 10-30 minutes after the contrast agent is injected, the myocardial function is lost, the contrast agent clearance is impaired, and it is detected by scanning that there is residual contrast agent. Consequently, a longitudinal relaxation time (T1) is significantly shortened, and a high signal is presented relative to normal myocardial tissue. In this way, the normal myocardial tissue and abnormal myocardial tissue are scanned 10-30 minutes after the injection of the contrast agent, and a contrast is formed and may be reflected in an image. The normal myocardial tissue has a relatively long longitudinal relaxation time T1, so that longitudinal relaxation recovery is slow. The abnormal myocardium loses activity and cannot clear the contrast agent, resulting in a relatively short longitudinal relaxation time T1 for infarcted myocardial tissue, so that longitudinal relaxation recovery is fast. The abnormal myocardium exhibits a high signal due to a short relaxation time T1, and thus enhanced (highlighted) display of the abnormal myocardium is implemented.

One great effect of the inversion recovery pulse, like a fat suppression or free water suppression sequence, is to selectively suppress a certain tissue by means of different zero crossing points of different tissues. Therefore, in myocardial delayed enhancement, a signal indicating that normal myocardial tissue is suppressed at a certain moment by the inversion recovery pulse may be utilized to implement enhanced (highlighted) display of the abnormal myocardium. By using the inversion recovery pulse, a magnetization vector can be inverted, an image signal can be recovered from −Mz to Mz, and if data is acquired at a zero crossing point of the normal myocardium, an image having the maximum contrast can be obtained. By determining an appropriate zero crossing point (zero return) time (nulling TI) of the normal myocardium and transmitting the inversion recovery pulse based on the TI, a normal myocardium signal will be suppressed—"blackened", and compared to the normal myocardium, an abnormal myocardium signal indicating residual gadolinium contrast agent will be significantly highlighted and enhanced.

As to how to determine the appropriate zero crossing point time of the normal myocardium, a group of multiple contrast images with different inversion times TI may be scanned, and which myocardial tissue signal is the lowest in this group of images may be obtained by comparison, to select a TI value corresponding to the image as the zero crossing point time of the normal myocardium.

A myocardial delayed enhancement sequence generally uses an inversion recovery sequence as a preparation pulse. The myocardial delayed enhancement sequence is briefly described below.

The myocardial delayed enhancement sequence includes at least an inversion recovery pulse and a sequence for signal acquisition (readout), and the sequence for signal acquisition includes a gradient echo (GRE) sequence or an echo planar imaging (EPI) sequence, etc., which is not limited in the embodiments of the present application. The inversion recovery pulse is generally a non-layer-selective (non-selective inversion recovery pulse), and the gradient echo sequence may include a fast gradient echo (FGRE) sequence, a spoiled gradient echo (SPGR) sequence, a fast balanced steady-state free precession (B-SSFP) imaging sequence, etc., which will not be illustrated one by one herein.

The myocardial delayed enhancement sequence includes a segmented myocardial delayed enhancement sequence, a segmented phase-sensitive myocardial delayed enhancement sequence, a multislice single-shot myocardial delayed enhancement sequence, and a multislice single-shot phase-sensitive myocardial delayed enhancement sequence, which will not be illustrated one by one herein, and will be described separately below.

Natural motions and flows (such as heart contraction and aortic blood flow) in a human body typically occur too quickly. Therefore, many MRI techniques segment signal acquisition, and a portion (or segment) of data is acquired at a high time resolution, to reduce the effects of the motions and flows on imaging. A time unit for acquiring a portion (or segment) of data may use, for example, a cardiac cycle as a unit. This time unit is referred to as a segment, and the acquisition is referred to as segmented acquisition. Such a segmented sequence is widely used throughout the body, particularly in the heart. For example, in cardiac MRI, only 20% of required data may be acquired in each cardiac cycle. For incomplete data, i.e., the other 80%, acquisition is completed in the next four cardiac cycles. For a segmented acquisition sequence, a plurality of cardiac cycle signals obtained through a plurality of times of acquisition are integrated to reconstruct one magnetic resonance image. Such applications include cardiac cine, myocardial delayed enhancement, black blood sequences, etc.

According to an aspect of the embodiments of the present application, a time sequence of the myocardial delayed enhancement sequence for each segment is characterized in that, to ensure the heart is imaged in the same phase during each signal acquisition, a gating technique is typically employed to synchronize signal acquisition with physiological motion. This gating technique, commonly used in magnetic resonance imaging (MRI), includes electrocardiogram (ECG) gating and finger pulse gating. In ECG gating, electrodes are placed on the subject's skin to detect weak electrical signals generated by the heart. These signals are then used to trigger or gate MRI signal acquisition, thereby synchronizing the acquisition with cardiac motion, such as the beating of the heart.

Figure 2:
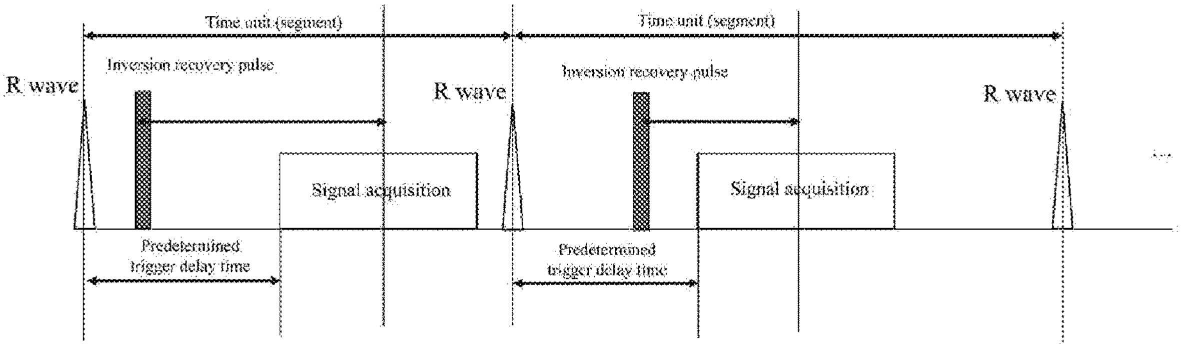
FIG. 2 is a time sequence diagram of a segmented myocardial delayed enhancement sequence according to an embodiment of the present application.

Therefore, as shown in FIG. 2, an electrocardiographic signal can be used for triggering. After an R wave is identified, an inversion recovery pulse is applied after a certain delay time, and longitudinal magnetization vectors of all tissues start to gradually recover. A sequence for signal acquisition is transmitted and signals are acquired. After a signal acquisition time ends, and after a next R wave is identified, the foregoing process is repeated. The time between the two R waves (also referred to as a cardiac cycle or an R-R interval) is used as a time unit, which can also be referred to as a segment. After signal acquisition of a plurality of segments is completed, a magnetic resonance image is reconstructed. In one time unit, an inversion time TI represents the time from the inversion recovery pulse to the middle of a filled K-space, or represents the time from the inversion recovery pulse to a signal acquisition center moment. The signal acquisition time may be set at a diastolic phase (resting phase) in the cardiac cycle, to minimize interference from the cardiac motion. For example, the signal acquisition time is started after a predetermined trigger delay time after an R wave is detected. It should be noted that the signal acquisition (readout) herein does not narrowly refer to acquiring signals by a receive coil, but includes a process of transmitting the sequence for signal acquisition and acquiring signals. The predetermined trigger delay (trigger delay) time and the signal acquisition time may be set according to experience, and the embodiments of the present application are not limited thereto.

Figure 3:
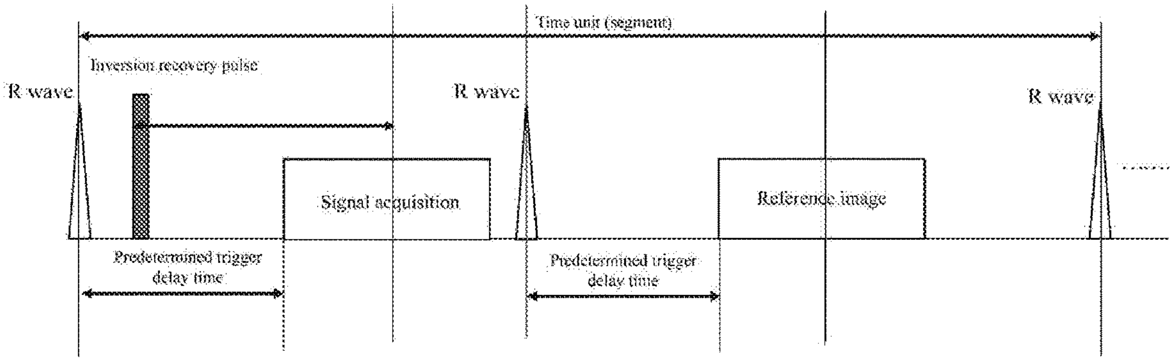
FIG. 3 is a time sequence diagram of a segmented phase-sensitive myocardial delayed enhancement sequence according to an embodiment of the present application.

In addition to the segmented myocardial delayed enhancement sequence, there is also a segmented phase-sensitive myocardial delayed enhancement sequence widely used at present, so that the setting of a Nulling TI can be more flexible, and the fault tolerance rate of Nulling TI selection is high. As shown in FIG. 3, a time unit of the segmented phase-sensitive myocardial delayed enhancement sequence may include two or three or more cardiac cycles. In a first cardiac cycle of the time unit, reference may be made to a segment of FIG. 2, and in a second cardiac cycle of the time unit, there is no need to transmit an inversion recovery pulse; instead, a pulse having a smaller flip angle than the sequence for signal acquisition in the first cardiac cycle is transmitted and a proton-density-like weighted reference image (phase reference) is acquired. Optionally (not shown in the figure), a time unit may further include a third cardiac cycle, and in the third cardiac cycle, no sequence transmission is required, no signal acquisition is required, and the third cycle is only used for recovery of a longitudinal magnetization vector. The foregoing process is repeated in each time unit, and finally, image reconstruction is performed by using a reference image, to obtain a phase-sensitive magnetic resonance image.

In addition to a segmented acquisition mode, there is a single-shot myocardial delayed enhancement sequence, which completes acquisition of all data of one layer in one cardiac cycle without segmented signal acquisition. Then, the foregoing process is repeated to scan all rows of the next layer, and so on, until scanning of all layers is completed. In this type of scan sequence, one time unit corresponds to a scan time of one layer, and the time unit may be one cardiac cycle or a plurality of cardiac cycles.

The single-shot phase-sensitive myocardial delayed enhancement sequence differs from the segmented phase-sensitive myocardial delayed enhancement sequence in that segmented signal acquisition is not required, and a magnetic resonance image of one layer can be obtained through one signal acquisition. A plurality of cardiac cycles may be included in the process of one signal acquisition, and for a specific processing means, reference may be made to the processing means of one time unit of the segmented phase-sensitive myocardial delayed enhancement sequence. Details are not described herein again.

The inventor found that a main challenge of myocardial delayed enhancement is arrhythmia or heart rate variability, the optimal inversion time of an inversion recovery pulse in the myocardial delayed enhancement is related to the heart rate, and since the heart rate changes in real time, it is necessary to dynamically update the inversion time. However, dynamically updating the inversion time at present is not applicable to all myocardial delayed enhancement sequences, such as a phase-sensitive myocardial delayed enhancement sequence and a single-shot myocardial delayed enhancement sequence. In view of at least one of the foregoing problems, the embodiments of the present application provide a magnetic resonance imaging method and a magnetic resonance imaging system. Description is made below in conjunction with the embodiments.

Figure 4:
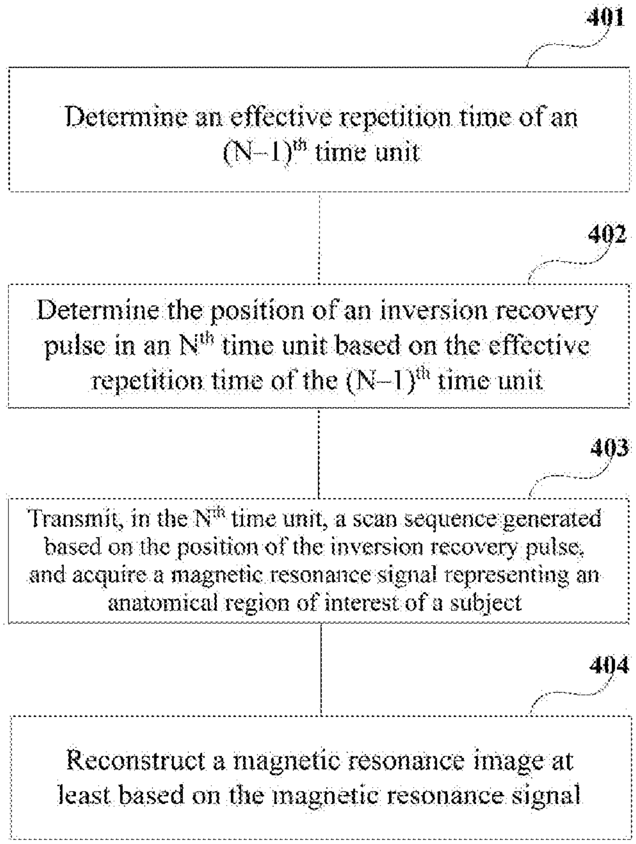
FIG. 4 is a schematic diagram of a magnetic resonance imaging method according to an embodiment of the present application.

The embodiments of the present application provide a magnetic resonance imaging method. The method is used to acquire, in a plurality of (Y, which is an integer greater than 2) consecutive time units, magnetic resonance signals representing one or more layers of an anatomical region of interest of a subject and generate a magnetic resonance image. FIG. 4 is a schematic diagram of a magnetic resonance imaging method according to an embodiment of the present application. As shown in FIG. 4, the method includes a step 401 for determining an effective repetition time of an $(N-1)^{th}$ time unit and step 402 for determining the position of an inversion recovery pulse in an $N^{th}$ time unit based on the effective repetition time of the $(N-1)^{th}$ time unit, wherein N is an integer greater than 1. The method also includes a step 403 for transmitting, in the $N^{th}$ time unit, a scan sequence generated based on the position of the inversion recovery pulse, and acquiring a magnetic resonance signal representing an anatomical region of interest of a subject. Finally step 404 includes reconstructing a magnetic resonance image at least based on the magnetic resonance signal.

In some embodiments, the anatomical region of interest of the subject includes, but is not limited to, anatomical sites such as the heart, the liver, the brain, and the lungs. In the embodiments of the present application, the heart is used as an example, but this embodiment of the present application is not limited thereto.

In some embodiments, the scan sequence includes at least one of the following sequences: a segmented myocardial delayed enhancement sequence; a segmented phase-sensitive myocardial delayed enhancement sequence; a multislice single-shot myocardial delayed enhancement sequence; and a multislice single-shot phase-sensitive myocardial delayed enhancement sequence. Implementations of the foregoing sequences are as described above. Details are not described herein again.

In some embodiments, the time unit includes one or more cardiac cycles, and one time unit corresponds to one segment or layer. For example, when the scan sequence is a segmented myocardial delayed enhancement sequence, each time unit includes one cardiac cycle, and each time unit corresponds to one segment. When the scan sequence is a segmented phase-sensitive myocardial delayed enhancement sequence, each time unit includes a plurality of cardiac cycles (for example, two), and each time unit corresponds to one segment. For example, when the scan sequence is a multislice single-shot myocardial delayed enhancement sequence, each time unit includes a plurality of cardiac cycles, and each time unit corresponds to one layer, which will not be illustrated one by one herein.

In some embodiments, before a formal diagnostic scan, the method may further include (not shown in the figure): estimating an apparent longitudinal relaxation time T1 of a first tissue of the anatomical region of interest. In the following, the anatomical region of interest being the heart and the first tissue being normal myocardial tissue is used as an example. The apparent longitudinal relaxation time T1 is not a real T1 of the normal myocardial tissue, but is estimated based on an inversion time of a zero crossing point of the normal myocardial tissue. The detailed description is provided below.

In some embodiments, before a formal diagnostic scan, an inversion time scout (TI Scout) sequence scan is performed to determine an inversion time (nulling TI) of a zero crossing point of the first tissue. For the TI scout sequence scan, reference may be made to the related art, and the embodiments of the present application are not limited thereto. After the TI scout sequence scan is performed, a target image is obtained, and a TI time corresponding to the darkest myocardium (the lowest signal) is determined, based on the target image, as the zero crossing point $TI_{null}$ of the first tissue (TI at which the first tissue is suppressed). However, the present application is not limited thereto, and the zero crossing point $TI_{null}$ of the first tissue may alternatively be obtained by another method. Details are not described herein again.

In some embodiments, the apparent longitudinal relaxation time T1 of the first tissue is estimated based on the inversion time of the zero crossing point of the first tissue. For example, the $TI_{null}$ at zero crossing point of the first tissue and the apparent T1 ($T1_{amyo}$) of the first tissue satisfy the following Formula (1):

$$TI_{null} = T1_{amyo} \cdot \left[\ln 2 - \ln\left(1 + e^{\frac{-TR_{eff}}{T1_{amyo}}}\right)\right] \quad \text{Formula (1)}$$

In the formula, $TR_{eff}$=#RR×1000×60/HR, HR represents a current heart rate or an estimated heart rate of the subject in beats per minute (BPM), and #RR is a number of heartbeats in one time unit. $TI_{null}$ and $TR_{eff}$ are substituted into Formula (1) to perform inverse solution, to obtain the apparent longitudinal relaxation time T1.

In some embodiments, the sequence pulse generator 133 may also receive data from the physiological acquisition controller 155, and the physiological acquisition controller receives electrocardiogram (ECG) signals from electrodes attached to the patient, and controls electrocardiogram gating in synchronization with the time unit to generate the scan sequence. For example, an electrocardiogram signal is used for triggering, and after an R wave is identified, scanning of a first time unit (a first segment or a first layer) is started, an effective repetition time of the first time unit is determined, and the position of an inversion recovery pulse in a second time unit is determined based on the effective repetition time of the first time unit. A scan sequence generated based on the position of the inversion recovery pulse is transmitted in the second time unit, and when an R wave is identified after the first time unit ends, scanning of the second time unit (a second segment or a second layer) is started, and so on, until scanning of all (Y) time units (all segments or all layers) is completed. A magnetic resonance image is reconstructed based on magnetic resonance signals acquired in all time units. The value of Y may be determined as required, for example, Y=4 or Y=10, etc., and the embodiments of the present application are not limited thereto. The foregoing process is described below by using the $(N-1)^{th}$ time unit and the $N^{th}$ time unit as an example.

In some embodiments, the effective repetition time is equivalent to the length of the $(N-1)^{th}$ time unit, which may also be referred to as an effective repetition time of the $(N-1)^{th}$ segment or the $(N-1)^{th}$ layer. The effective repetition time of the $(N-1)^{th}$ time unit is equal to the time of one or more cardiac cycles. Because the length of the cardiac cycle of the subject is variable, and some effective repetition times include a plurality of cardiac cycles (e.g., phase-sensitive myocardial delayed enhancement sequences), if the length of the cardiac cycle is measured by using an external device, there may be a lag of tens to hundreds of milliseconds, and it is difficult to promptly update the position of the inversion recovery pulse in the $N^{th}$ time unit. For at least one of the foregoing problems, the embodiments of the present application propose to determine the effective repetition time of the $(N-1)^{th}$ time unit on the basis of a cardiac cycle timing method, which is described in detail below with reference to FIG. 5.

Figure 5:
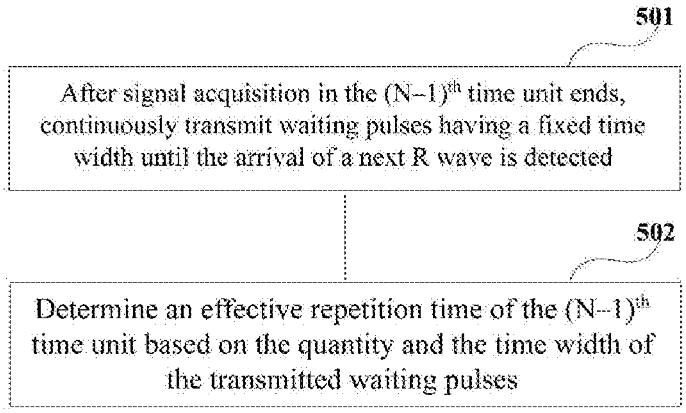
FIG. 5 is a schematic diagram of an implementation of step 401 according to an embodiment of the present application.

FIG. 5 is a schematic diagram of an implementation of step 401 according to an embodiment of the present application. As shown in FIG. 5, the method includes: at step 501, after signal acquisition in the $(N-1)^{th}$ time unit ends, continuously transmitting waiting pulses having a fixed time width until the arrival of a next R wave is detected. The method also includes a step 502 for determining the effective repetition time of the $(N-1)^{th}$ time unit based on the quantity and the time width of the transmitted waiting pulses.

Figure 6:
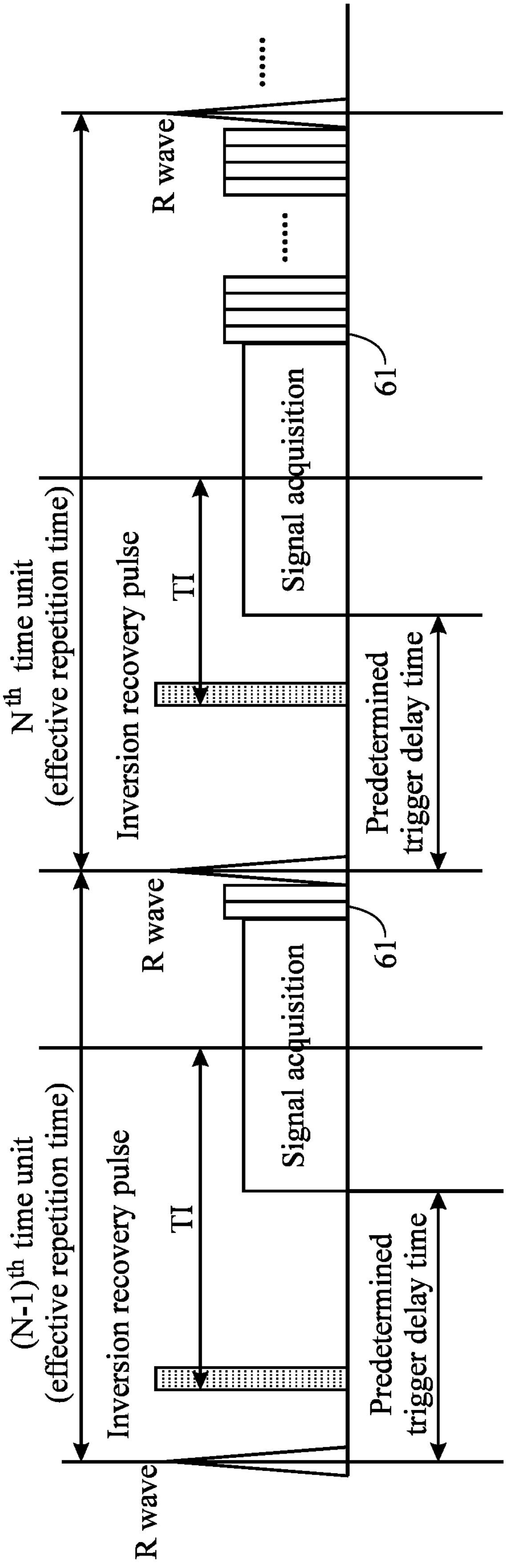
FIG. 6 is a time sequence diagram of a scan sequence according to an embodiment of the present application.

FIG. 6 is a time sequence diagram of waiting pulses according to an embodiment of the present application. As shown in FIG. 6, one time unit corresponding to one cardiac cycle is used as an example. When an R wave is detected, the $(N-1)^{th}$ time unit is started. Signal acquisition is started after a predetermined trigger delay time after the R wave is detected. Continuous transmission of waiting pulses 61 having a fixed time width is started after the signal acquisition ends. The transmission of the waiting pulses is stopped when the arrival of a next R wave is detected.

Figure 7:
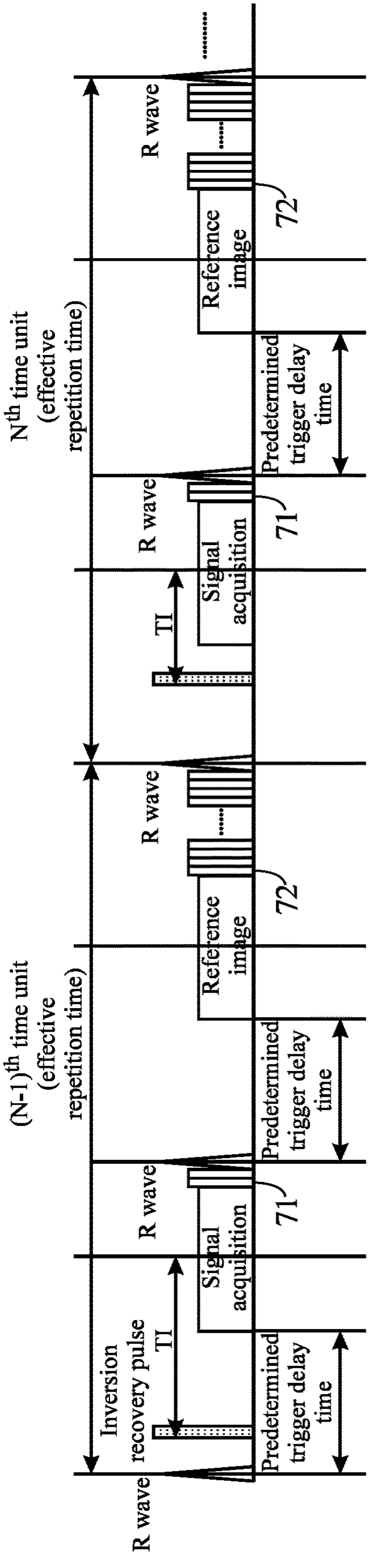
FIG. 7 is a time sequence diagram of a scan sequence according to an embodiment of the present application.

FIG. 7 is a time sequence diagram of waiting pulses according to an embodiment of the present application. As shown in FIG. 7, one time unit corresponding to two cardiac cycles is used as an example. When an R wave is detected, the $(N-1)^{th}$ time unit is started. Signal acquisition is started after a predetermined trigger delay time after a first R wave is detected. Continuous transmission of waiting pulses 71 having a fixed time width is started after the signal acquisition ends. The transmission of the waiting pulses is stopped when the arrival of a next R wave is detected. After the predetermined trigger delay time, by using a pulse having a smaller flip angle and acquiring a proton-density-like weighted reference image, after the reference image is obtained, continuous transmission of waiting pulses 72 is started until the arrival of a third R wave is detected.

In some embodiments, the fixed time width of the waiting pulses is preset, and the time width may be set to be relatively small. The quantity of transmitted waiting pulses is counted, and a trigger delay time is predetermined based on the product of the quantity and the time width. The effective repetition time may be determined by the time of the signal acquisition. For example, for the sequence in FIG. 6, the product of the quantity of waiting pulses and the time width is S1, the predetermined trigger delay time is D1, the time for the signal acquisition is R1, and the effective repetition time is equal to S1+D1+R1. For the sequence in FIG. 7, the product of the quantity of waiting pulses of the first cardiac cycle and the time width is S1, the predetermined trigger delay time is D1, the time for the signal acquisition is R1, the product of the quantity of waiting pulses of the second cardiac cycle and the time width is S2, the predetermined trigger delay time is D2, an acquisition time of the reference image is R2, and the effective repetition time is equal to S1+S2+D1+D2+R1+R2.

It can be learned from the foregoing embodiments that an effective repetition time of a time unit is not measured by an external device, but is calculated based on a sequence time sequence. The method has a fast response speed, and can determine the effective repetition time in real time without measurement by an external device, and promptly update the position of the inversion recovery pulse in the $N^{th}$ time unit.

In some embodiments, in 402, the position of the inversion recovery pulse in the $N^{th}$ time unit may be determined based on the apparent longitudinal relaxation time T1 and the effective repetition time of the $(N-1)^{th}$ time unit. The inversion time in the $N^{th}$ time unit is first determined based on the effective repetition time of the $(N-1)^{th}$ time unit and the apparent longitudinal relaxation time T1, and the inversion time is positively correlated with both the apparent longitudinal relaxation time T1 ($T1_{amyo}$) and the effective repetition time of the $(N-1)^{th}$ time unit $$TR_{eff}^{n-1}.$$

Inversion times of different time units are dynamically variable, not fixed.

In some embodiments, the inversion time in $$TI_{dyn}^{n}$$

the $N^{th}$ time unit may be determined according to the following Formula (2):

$$TI_{dyn}^{n} = T1_{amyo} \cdot \left[\ln 2 - \ln\left(1 + e^{\frac{-TR_{eff}^{n-1}}{T1_{amyo}}}\right)\right] \quad \text{Formula (2)}$$

The foregoing are only examples for description, and the embodiments of the present application are not limited thereto. For example, the inversion time $$TI_{dyn}^{n}$$

in the $N^{th}$ time unit may alternatively be determined according to the following Formula (3).

$$TI_{dyn}^{n} = T1_{amyo} \cdot \left[\ln 2 - \ln\left(1 + e^{\frac{-TR_{eff}^{avg}}{T1_{amyo}}}\right)\right] \quad \text{Formula (3)}$$

Formula (3) differs from Formula (2) in that $$TR_{eff}^{avg}$$

is not equal to the effective repetition time of the $(N-1)^{th}$ time unit, but is determined based on the effective repetition time of the $(N-1)^{th}$ time unit. However, $$TR_{eff}^{avg}$$

may be equal to a weighted average value of effective repetition times of X time units. The X time units are X time units before the $N^{th}$ time unit, and include the effective repetition time of the $(N-1)^{th}$ time unit, wherein X is an integer greater than or equal to 2. For example, when X=2, $$TR_{eff}^{avg}$$

is equal to a weighted average value of the effective repetition time of the $(N-1)^{th}$ time unit and an effective repetition time of an $(N-2)^{th}$ time unit, which will not be illustrated one by one herein.

It should be noted that the inversion time of the first time unit during a diagnostic scan may be a preset inversion time, or may be determined based on an effective repetition time of the last time unit in a dummy scan before the diagnostic scan in combination with the foregoing Formula (2) or Formula (3). The embodiments of the present application are not limited thereto. Scan sequences and set parameters of the dummy scan are completely consistent with those of the diagnostic scan, and the dummy scan differs from the diagnostic scan in that no image needs to be reconstructed in the dummy scan. Therefore, an inversion time in each time unit during the dummy scan may also be determined by using the foregoing implementations. Details are not described herein again.

In some embodiments, the inversion time $$TI_{dyn}^{n}$$

is a time length between a moment at which the inversion recovery pulse is transmitted and a signal acquisition center moment in the $N^{th}$ time unit. Therefore, the position of the inversion recovery pulse in the $N^{th}$ time unit may be determined based on the inversion time. In one time unit, the signal acquisition center moment TC may be determined based on a time when an R wave is detected and the predetermined trigger delay time, and in the $N^{th}$ time unit, the moment at which the inversion recovery pulse is transmitted is $$TC - TI_{dyn}^{n}.$$

In some embodiments, the inversion recovery pulse is transmitted at the moment $$TC - TI_{dyn}^{n}$$

in the $N^{th}$ time unit, and signal acquisition is performed after a predetermined trigger time of the R wave, to obtain a magnetic resonance signal representing the anatomical region of interest of the subject in the $N^{th}$ time unit. When the scan sequence is a segmented myocardial delayed enhancement sequence, image reconstruction is completed after magnetic resonance signals of all segments are obtained. When the scan sequence is a single-shot myocardial delayed enhancement sequence, a magnetic resonance image of an $N^{th}$ layer can be reconstructed when the magnetic resonance signal in the $N^{th}$ time unit is obtained.

Figure 8:
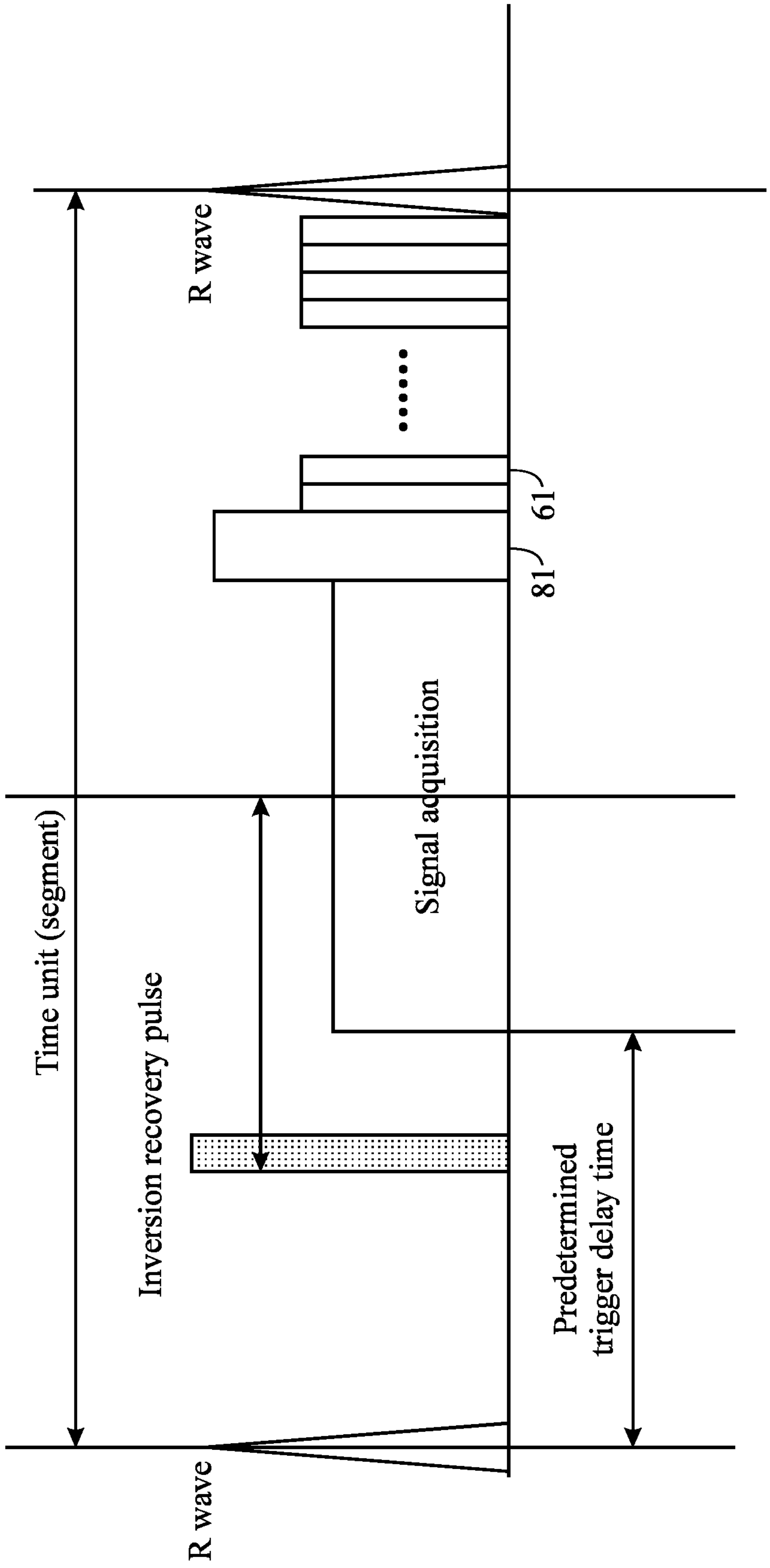
FIG. 8 is a time sequence diagram of a scan sequence according to an embodiment of the present application.

In some embodiments, as shown in FIG. 8, one time unit is used as an example, the scan sequence may further include a saturation recovery (SR) erasing pulse 81 transmitted after the signal acquisition time, and the saturation recovery erasing pulse is an optional pulse. The saturation recovery erasing pulse can remove the history of a longitudinal magnetization vector Mz, which helps to reduce oscillation of Mz, especially for a tissue having a long T1. In addition, the erasing pulse is not only insensitive to heart rate changes, but also can reduce the number of dummy scans and thus shorten a scanning time/breath-holding time, thereby further improving the image quality.

In some embodiments, when the scan sequence includes the saturation recovery erasing pulse, as shown in FIG. 8, the aforementioned waiting pulses may be transmitted after the signal acquisition in the $(N-1)^{th}$ time unit ends and the saturation recovery erasing pulse ends. Details are not described herein again.

In some embodiments, if switching to a next scan subject to be scanned, then the aforementioned imaging method is performed again.

Figure 9:
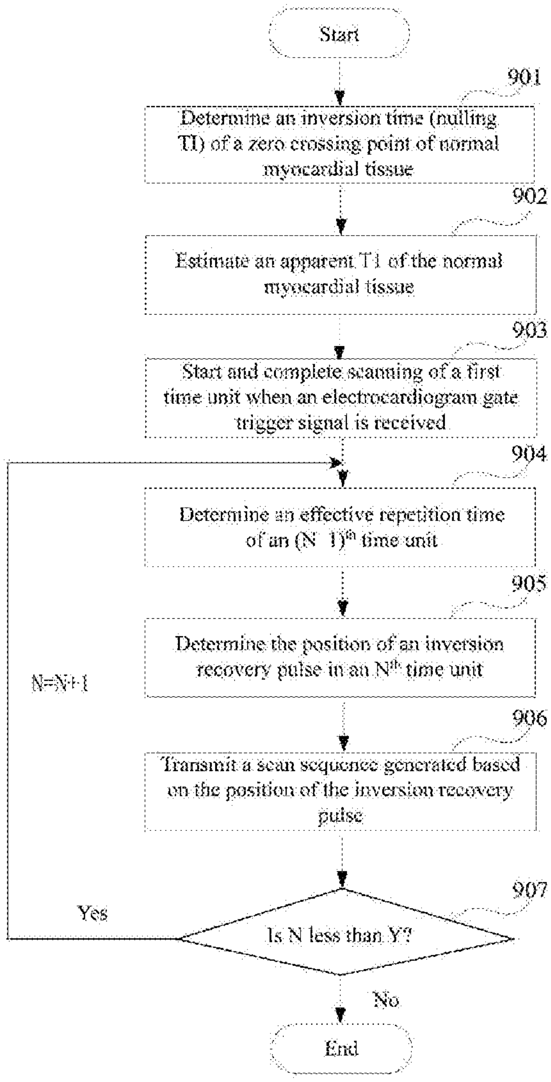
FIG. 9 is a flowchart of a magnetic resonance imaging method according to an embodiment of the present application.

According to an embodiment of the present application, a magnetic resonance imaging method is provided, as illustrated in FIG. 9. The method begins, at step 901, by performing an inversion time scout (TI Scout) sequence scan to determine an inversion time (nulling TI) corresponding to the zero crossing point of normal myocardial tissue. At step 902, an apparent longitudinal relaxation time T1 of the normal myocardial tissue is estimated based on the inversion time determined in step 901. At step 903, scanning of a first time unit is initiated and completed upon receipt of an electrocardiogram (ECG) gate trigger signal. At step 904, an effective repetition time of an $(N-1)^{th}$ time unit is determined, where the initial value of N is 2.

At step 905, the position of an inversion recovery pulse in an $N^{th}$ time unit is determined based on the effective repetition time of the $(N-1)^{th}$ time unit and the apparent longitudinal relaxation time T1 estimated in step 902. At step 906, a scan sequence is transmitted in the $N^{th}$ time unit, the sequence being generated based on the position of the inversion recovery pulse, and a magnetic resonance signal representing the anatomical region of interest is acquired. At step 907, it is determined whether N is less than Y. If N is less than Y, N is incremented by 1 (N=N+1), and the process returns to step 904. If N equals Y, the scanning process is concluded.

Specific implementations of steps 901 to 907 are as previously described and are not repeated herein. The foregoing steps 901 to 907 may be applied to a dummy scan or a formal diagnostic scan, and the embodiments of the present application are not limited thereto. When the foregoing steps are applied to a formal diagnostic scan, a magnetic resonance image may further be reconstructed based on the acquired magnetic resonance signals. Details are not described herein again.

By means of the foregoing embodiments, the position of the inversion recovery pulse in the $N^{th}$ time unit is determined based on the effective repetition time of the $(N-1)^{th}$ time unit. Therefore, dynamic updating of inversion times (TI) of various types of myocardial delayed enhancement sequences is supported, so that the sequences are not easily affected by heartbeat fluctuations or heart rate abnormalities, ghosting is reduced, and a myocardial suppression effect and image quality are improved.

Figure 10:
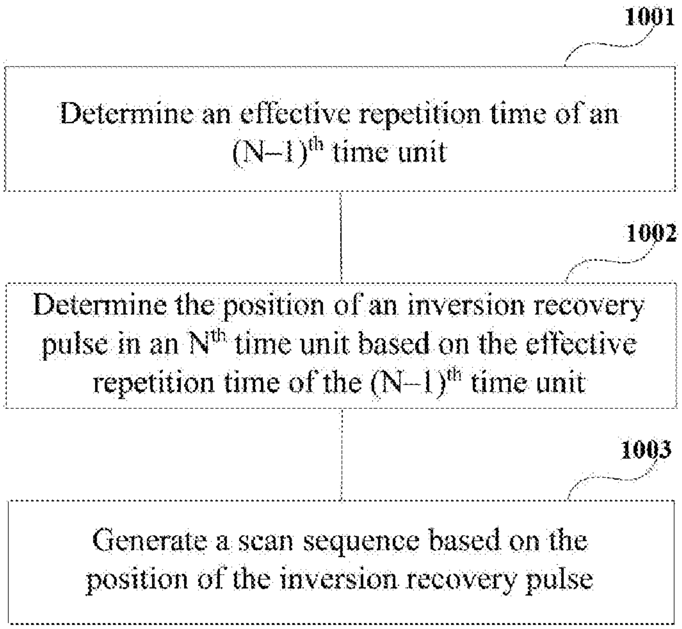
FIG. 10 is a schematic diagram of a scan sequence generation method according to an embodiment of the present application.

According to embodiments of the present application, a scan sequence generation method is provided, as illustrated in FIG. 10. The method includes the following steps: at step 1001, determining an effective repetition time of an $(N-1)^{th}$ time unit; at step 1002, determining the position of an inversion recovery pulse in an $N^{th}$ time unit based on the effective repetition time of the $(N-1)^{th}$ time unit; and at step 1003, generating a scan sequence based on the position of the inversion recovery pulse.

Implementations of steps 1001 to 1003 are as described above. Details are not described herein again.

The embodiments of the present application further provide a magnetic resonance imaging system. The configuration of the magnetic resonance imaging system is as shown in FIG. 1, and similarities are not repeated here.

In some embodiments, unlike the foregoing magnetic resonance imaging system in FIG. 1, the controller 130 is configured to perform the foregoing magnetic resonance imaging method.

In some embodiments, the controller 130 (which may alternatively be a processor) includes a computer processor and a storage medium. The storage medium has recorded thereon a predetermined data processing program to be executed by the computer processor. For example, the storage medium may store a program used to implement scanning processing (e.g., including waveform design/conversion, etc.), image reconstruction, image processing, etc. For example, the storage medium may store a program used to implement the scan sequence generation method in the embodiments of the present invention. Specific implementations thereof are as described above. Details are not described herein again.

The described storage medium may include, for example, a ROM, a floppy disk, a hard disk, an optical disk, a magneto-optical disk, a CD-ROM, or a non-volatile memory card.

Further provided in the embodiments of the present application is a computer-readable program, where the program, when executed in an apparatus or an MRI system, causes a computer to execute, in the apparatus or the MRI system, the method according to the foregoing embodiments.

Further provided in the embodiments of the present application is a storage medium having a computer-readable program stored therein, where the computer-readable program causes a computer to execute, in an apparatus or an MRI system, the method according to the foregoing embodiments.

The above apparatus and method of the present application can be implemented by hardware, or can be implemented by hardware in combination with software. The present application relates to such a computer-readable program that when executed by a logic component, the program causes the logic component to implement the foregoing apparatus or a constituent component, or causes the logic component to implement various methods or steps as described above. The present application further relates to a storage medium for storing the above program, such as a hard disk, a disk, an optical disk, a DVD, a flash memory, etc.

The method/apparatus described in view of the embodiments of the present application may be directly embodied as hardware, a software module executed by a processor, or a combination of the two. For example, one or more of the functional block diagrams and/or one or more combinations of the functional block diagrams shown in the drawings may correspond to either respective software modules or respective hardware modules of a computer program flow. The foregoing software modules may respectively correspond to the steps shown in the figures. The foregoing hardware modules can be implemented, for example, by firming the software modules using a field-programmable gate array (FPGA).

The software modules may be located in a RAM, a flash memory, a ROM, an EPROM, an EEPROM, a register, a hard disk, a portable storage disk, a CD-ROM, or any other form of storage medium known in the art. The storage medium may be coupled to a processor, so that the processor can read information from the storage medium and can write information into the storage medium. Alternatively, the storage medium may be a constituent component of the processor. The processor and the storage medium may be located in an ASIC. The software module may be stored in a memory of a mobile terminal, and may also be stored in a memory card that can be inserted into a mobile terminal. For example, if a device (such as a mobile terminal) uses a large-capacity MEGA-SIM card or a large-capacity flash memory apparatus, the software modules can be stored in the MEGA-SIM card or the large-capacity flash memory apparatus.

One or more of the functional blocks and/or one or more combinations of the functional blocks shown in the accompanying drawings may be implemented as a general-purpose processor, a digital signal processor (DSP), an application-specific integrated circuit (ASIC), a field-programmable gate array (FPGA) or other programmable logic devices, discrete gate or transistor logic devices, a discrete hardware assembly, or any appropriate combination thereof for implementing the functions described in the present application. The one or more functional blocks and/or the one or more combinations of the functional blocks shown in the accompanying drawings may also be implemented as a combination of computing devices, such as a combination of a DSP and a microprocessor, multiple microprocessors, one or more microprocessors in communication combination with a DSP, or any other such configuration.

The present application is described above with reference to specific implementations. However, it should be clear to those skilled in the art that the foregoing description is merely illustrative and is not intended to limit the scope of protection of the present application. Various variations and modifications may be made by those skilled in the art according to the principle of the present application, and said variations and modifications also fall within the scope of the present application.

The invention claimed is:

1. A magnetic resonance imaging method, comprising:

determining an effective repetition time of an $(N-1)^{th}$ time unit of a plurality of consecutive time units;

determining a position of an inversion recovery pulse in an $N^{th}$ time unit based on the effective repetition time of the $(N-1)^{th}$ time unit, wherein N is an integer greater than 1;

transmitting, in the $N^{th}$ time unit, a scan sequence generated based on the position of the inversion recovery pulse, and acquiring a magnetic resonance signal representing an anatomical region of interest of a subject; and reconstructing a magnetic resonance image at least based on the magnetic resonance signal, wherein each time unit of the plurality of consecutive time units comprises one or more cardiac cycles, and the effective-repetition time of the $(N-1)^{th}$ time unit is determined in real time based on a cardiac cycle timing method, and wherein determining the effective-repetition time of the $(N-1)^{th}$ time unit in real time based on the cardiac cycle timing method comprises:

after signal acquisition in the $(N-1)^{th}$ time unit ends, continuously transmitting waiting pulses having a fixed time width until an arrival of a next R wave is detected; and determining the effective repetition time of the $(N-1)^{th}$ time unit based on a quantity and the fixed time width of the transmitted waiting pulses.

2. The method according to claim 1, further comprising:

estimating an apparent longitudinal relaxation time of a first tissue of the anatomical region of interest; and determining the position of the inversion recovery pulse in the $N^{th}$ time unit based on the apparent longitudinal relaxation time and the effective-repetition time of the $(N-1)^{th}$ time unit.

3. The method according to claim 2, wherein the step of estimating the apparent longitudinal relaxation time of the first tissue of the anatomical region of interest comprises:

performing an inversion time scout sequence scan to determine an inversion time of a zero crossing point of the first tissue; and estimating the apparent longitudinal relaxation time of the first tissue based on the inversion time of the zero crossing point of the first tissue.

4. The method according to claim 1, wherein the determining the position of the inversion recovery pulse in the $N^{th}$ time unit based on the effective repetition time of the $(N-1)^{th}$ time unit comprises:

determining an inversion time in the $N^{th}$ time unit based on the effective repetition time of the $(N-1)^{th}$ time unit, wherein the inversion time is a time length between a transmission of the inversion recovery pulse and a signal acquisition center moment in the $N^{th}$ time unit; and determining the position of the inversion recovery pulse in the $N^{th}$ time unit based on the inversion time.

5. The method according to claim 4, wherein the inversion time is positively correlated with the effective repetition time.

6. The method according to claim 1, wherein the scan sequence comprises at least one of the following sequences:

a segmented myocardial delayed enhancement sequence;

a segmented phase-sensitive myocardial delayed enhancement sequence;

a multislice single-shot myocardial delayed enhancement sequence; and a multislice single-shot phase-sensitive myocardial delayed enhancement sequence.

7. The method according to claim 1, wherein the scan sequence further comprises a saturation recovery erasing pulse transmitted after a signal acquisition time.

8. A magnetic resonance imaging system, comprising:

a scanning unit; and a controller configured to:

determine an effective repetition time of an $(N-1)^{th}$ time unit of a plurality of consecutive time units;

determine a position of an inversion recovery pulse in an $N^{th}$ time unit based on the effective repetition time of the $(N-1)^{th}$ time unit, wherein N is an integer greater than 1;

transmit, in the $N^{th}$ time unit, a scan sequence generated based on the position of the inversion recovery pulse, and acquiring a magnetic resonance signal representing an anatomical region of interest of a subject; and reconstruct a magnetic resonance image at least based on the magnetic resonance signal, wherein each time unit of the plurality of consecutive time units comprises one or more cardiac cycles, and the effective-repetition time of the $(N-1)^{th}$ time unit is determined in real time based on a cardiac cycle timing method, and wherein to determine the effective-repetition time of the $(N-1)^{th}$ time unit in real time based on the cardiac cycle timing method, the controller is further configured to:

after signal acquisition in the $(N-1)^{th}$ time unit ends, continuously transmit waiting pulses having a fixed time width until an arrival of a next R wave is detected; and determine the effective repetition time of the $(N-1)^{th}$ time unit based on a quantity and the fixed time width of the transmitted waiting pulses.

9. The system according to claim 8, wherein the controller is further configured to:

estimate an apparent longitudinal relaxation time of a first tissue of the anatomical region of interest; and determining the position of the inversion recovery pulse in the $N^{th}$ time unit based on the apparent longitudinal relaxation time and the effective-repetition time of the $(N-1)^{th}$ time unit.

10. The system according to claim 9, wherein to estimate the apparent longitudinal relaxation time of the first tissue of the anatomical region of interest, the controller is further configured to:

perform an inversion time scout sequence scan to determine an inversion time of a zero crossing point of the first tissue; and estimating the apparent longitudinal relaxation time of the first tissue based on the inversion time of the zero crossing point of the first tissue.

11. The system according to claim 8, wherein to determine the position of the inversion recovery pulse in the $N^{th}$ time unit based on the effective repetition time of the $(N-1)^{th}$ time unit, the controller is further configured to:

determine an inversion time in the $N^{th}$ time unit based on the effective repetition time of the $(N-1)^{th}$ time unit, wherein the inversion time is a time length between a transmission of the inversion recovery pulse and a signal acquisition center moment in the $N^{th}$ time unit; and determine the position of the inversion recovery pulse in the $N^{th}$ time unit based on the inversion time.

12. The system according to claim 11, wherein the inversion time is positively correlated with the effective repetition time.

13. The system according to claim 8, wherein the scan sequence comprises at least one of the following sequences:

a segmented myocardial delayed enhancement sequence;

a segmented phase-sensitive myocardial delayed enhancement sequence;

a multislice single-shot myocardial delayed enhancement sequence; and a multislice single-shot phase-sensitive myocardial delayed enhancement sequence.

14. The system according to claim 8, wherein the scan sequence further comprises a saturation recovery erasing pulse transmitted after a signal acquisition time.

* * * * *